United States Patent [19]

Wendorff

[11] 4,037,603
[45] July 26, 1977

[54] METALLIC SURGICAL SUTURE

[76] Inventor: Erwin R. Wendorff, 1303 Garden Lane, Reading, Pa. 19602

[21] Appl. No.: 576,960

[22] Filed: May 13, 1975

[51] Int. Cl.² .............................................. A61B 17/04
[52] U.S. Cl. ................................................. 128/335.5
[58] Field of Search ................... 128/326, 327, 334 R, 128/334 C, 335, 335.5; 40/21 R, 21 C; 63/3; 24/16 PB, 20 R, 20 CW, 20 EE, 30.5 P, 30.5 S, 206 A, 17 A

[56] References Cited

U.S. PATENT DOCUMENTS

| | | | |
|---|---|---|---|
| 1,824,199 | 9/1931 | Donohoe | 40/21 R |
| 2,870,502 | 1/1959 | Sasse | 24/17 A |
| 2,961,785 | 11/1960 | Toepfer | 40/21 R |
| 3,224,054 | 12/1965 | Lige | 24/16 PB |
| 3,540,452 | 11/1970 | Usher | 128/335.5 |
| 3,570,497 | 3/1971 | Lemole | 128/335.5 |
| 3,729,007 | 4/1973 | Mirkovitch | 128/335.5 |
| 3,785,337 | 1/1974 | Flowerday | 40/21 R X |

*Primary Examiner*—Richard J. Apley
*Attorney, Agent, or Firm*—Miller & Prestia

[57] ABSTRACT

A suture of a type particularly adaptable for employment for operations such as that referred to as "urethrovaginal fixation to Cooper's ligament in the treatment of stress incontinence." The suture is employed in the form of a loop with its end portions in interlocking engagement. The suture comprises an elongated, flexible, plastic-coated, thin steel band penetrated by longitudinal series of rectangular apertures with their greater dimensions extending longitudinally of the band. Both ends of the band have projecting shouldered tongues normally lying in the plane of the band. When the suture is formed into a loop with the end portions thereof in overlapping relationship, as occurs during the final stages of an operation such as that referred to above, the tongue at the end of the overlapping portion is twisted from its planar position and inserted in a selected aperture of the underlapping portion. Similarly, the tongue at the end of the underlapping portion is twisted and inserted in an aperture of the overlapping portion. In each case, after the insertion of the tongue, it is restored to its planar position with its shoulders contacting the face of the band.

5 Claims, 6 Drawing Figures

U.S. Patent      July 26, 1977      4,037,603

METALLIC SURGICAL SUTURE

BACKGROUND OF THE INVENTION

1. Field of the Invention

The invention concerns improved sutures particularly adaped for employment in operations such as that entitled "urethrovaginal fixation to Cooper's ligament for correction of recurrent stress incontience". It will be understood, however, that use of the suture is not limited to such operations.

2. Description of the Prior Art

Heretofore in operations such as referred to above and as described in an article entitled "Urethrovaginal Fixation to Cooper's Ligament (Burch) in the Treatment of Incontinence" by Erfurth Nielsen and Finn Lundval of Copenhagen, Denmark, the article having been published in Acta Scand. Suppl. 433: 118 –120, 1973, and copies of the article being available in medical libraries, have involved the use of three or more sutures of catgut on each side of Cooper's ligament which are passed through the perivaginal fascia on each side of the urethra after dissection of the space of Retzius and adequate exposure of the bladder and urethra. Each suture is then passed through the most easily reached point of Cooper's ligament and tied.

The above procedure has presented serious problems as, for example, the procedure is very time-consuming for the surgeon and the patient is exposed for an excessive period of trauma. Also, the sutures do not necessarily uniformly distribute the stress as in many instances some will be tighter than others. In addition, it has been found that in a number of instances the sutures break if the patient should have a coughing spell or be subject to other spasms.

SUMMARY OF THE INVENTION

The principal object of the instant invention is the provision of a suture which eliminates the problems heretofore encountered in operations such as that entitled "Urethrovaginal fixation to Cooper's ligament in the treatment of incontinence."

Another object of the present invention is the provision of a suture for use in the operation referred to in the foregoing object, and which is also adaptable for use in other operations, in which both ends of the suture may be individually interlocked with the body portion thereof providing increased safety and maintenance of the suture in place.

Another object of the invention is the provision of a suture attaining the foregoing objects which is simple in design and economical to manufacture.

A further object of the invention is the provision of a suture which is very flexible and malleable made from surgical steel and which may be employed as a single suture in substitution for a plurality of sutures as previously required in certain operations.

The foregoing and other objects of the invention, will become apparent, are attained by the suture of the instant invention and the method of its employment, the suture comprising a highly flexible, preferably plastic-coated, elongated strip of surgical steel having means for interlocking both ends of the suture with a body portion thereof in selected positions. The locking means suitably includes two series of elongated rectangular apertures in the body portion of the strip, one series extending from one end of an unapertured intermediate section of the body portion of the strip to a point relatively adjacent one end of the strip and the other leading from the other end of said intermediate section to a point relatively adjacent the other end of the strip. Each end of the strip has a projecting tongue comprising an outer end portion suitably of substantially the width of the body portion of the strip. Each end portion is connected to the body portion by a neck in alignment with and having a portion of somewhat less width than the widths of the apertures in the body portion, the necks defining shoulders on the end portions.

In the employment of the suture, the surgeon, following the insertion of the suture, brings one end portion into overlapping relationship with the other. The tongue at the end of the overlapping portion is twisted from a planar portion approximately 90° and inserted relatively perpendicularly into a selected one of the perforations of the underlapping portion of the suture. The tongue at the end of the underlapping portion is similarly twisted approximately 90° and inserted in an aperture of the overlapping portion of the suture. Following the insertion of the tongue in each case, it is restored to a planar position with its shoulders contacting the face of the band.

Figure 1:
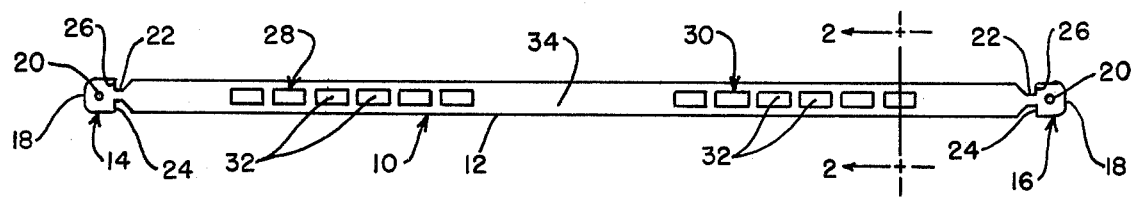
FIG. 1 is a plan view of a suture in accordance with the instant invention.
Figure 3:
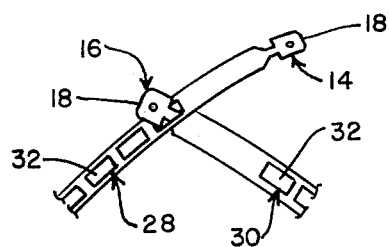
FIG. 3 is a diagrammatic perspective view with parts broken away of the suture of FIG. 1 at one stage in the interlocking of one end thereof to the body portion following the insertion of the suture.

Referring now to the drawings and particularly to FIG. 1, the suture of the invention which is indicated generally by the reference character 10 consists of an elongated, flexible strip of surgical steel, such steel preferably being of the ASTM designation F138-71 316 LC. The suture has an elongated body portion 12 and integral tongues 14 and 16 projecting outwardly from the opposite ends thereof. The body portion 12 is suitably of a length of the order of 12.5 cm., a width of the order of 5 mm., and a thickness of the order of 0.15 mm. Tongues 14 and 16 each include a head portion 18 having a perforation 20, the head portions, suitably of a width and thickness corresponding to the body portion, being integrally connected by parallel-sided necks 22 to partially rounded end portions of the body portion 12. The necks together with the heads define shoulders 24 and 26. The widths of the heads 18 and the thickness of the metal constituting the same are suitably but not necessarily the same width and thickness respectively for the body portion 12. As illustrated, the outer ends of the heads 18 are preferably rounded or otherwise shaped for ready insertion in apertures of the body portion now to be described.

The body portion suitably contains two spaced series 28 and 30 of apertures 32, one series 28 extending from a point relatively adjacent one end of the body portion to one end of an unapertured intermediate portion 34 of the body portion and the other series 30 extending from a point relatively adjacent the other end of the body portion to the other end of the unapertured intermediate portion. Each aperture 32 is of a length to readily permit the penetration therethrough of a tongue 14 or 16 when the tongue is turned, by the twisting of the body portion adjacent to the tongue, to bring the tongue into approximately right angular relationship to the body portion and in overlying or underlying relationship to a selected one of the apertures. Also, each aperture 32 is of a width somewhat greater than the width of the necks 22 of the tongues 14 and 16 to readily accomodate the necks when the tongues are restored to planar positions following their insertion in the apertures. For example, to accomodate tongues having the dimensions previously referred to, the apertures are suitably of a length of 5.5 mm. and a width of 2.5 mm.

Figure 2:
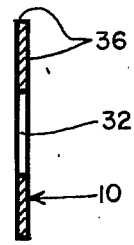
FIG. 2 is a sectional view on an enlarged scale taken on the line 2 —2 of FIG. 1 looking in the direction indicated by the arrows.
Figure 4:
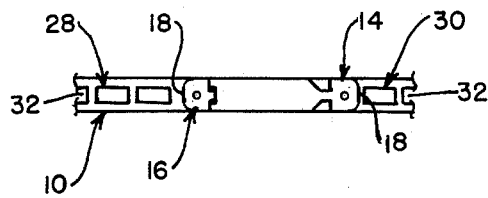
FIG. 4 is a view similar to FIG. 3 illustrating the suture at the final or completed state in the interlocking of said one end with the body portion.
Figure 5:
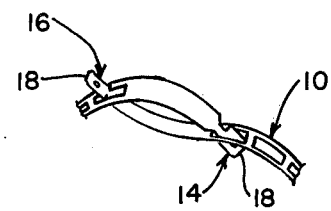
FIG. 5 is a diagrammatic perspective view with parts broken away illustrating the suture of FIG. 1 at one stage in the interlocking of the second end thereof to the body portion.
Figure 6:
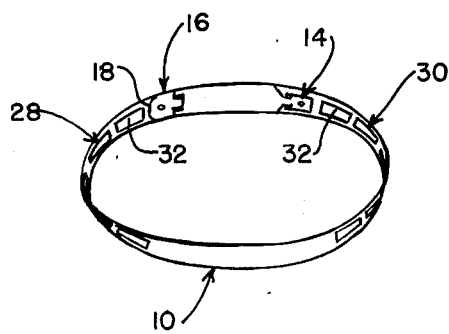
FIG. 6 is a view similar to FIG. 5 illustrating the final or completed state in the interlocking of said second end to the body portion.

Following the conversion of the metal strip material into the suture illustrated in FIG. 1, a relatively thin plastic coating is suitably applied to all portions of the suture. A preferred plastic coating for this purpose is silicone type A, represented, for example, by that marketed by the Dow-Corning Chemical Corporation of Corning, N.Y., under the mark "Selastic Medical Adhesive." The plastic coating is illustrated in FIG. 2 where it is identified by reference character 36.

The employment of the suture of the instant invention as, for example, in the operation previously referred to, namely "urethrovaginal fixation to Cooper's ligament in the treatment of incontinence," and the manner of interlocking the tongues 14 and 16 with apertures 32 of the body portion 12 will now be described. Following the making of an incision by the surgeon extending laterally between the pelvic bones of the patent and the surgeon's performance of further preparatory steps, he inserts the suture through one side of Cooper's ligament supporting the urethra and out the other side. In order to expedite the insertion, the surgeon may employ a conventional catgut suture which is passed through the perforation 20 in the tongue at the leading end of the suture 10, the catgut suture serving as a pulling or drawing means. The catgut suture is removed when the insertion has been completed. Following insertion of the suture, the extending ends are placed in lapping relationship. Referring now particularly to FIGS. 3-6 inclusive which are diagrammatic views and do not include a showing of any part of the patient's body, an end portion of the underlapping portion of the suture and the tongue carried thereby, namely tongue 16 as shown in the Figures, are twisted approximately 90°, and the head 18 of the tongue is inserted approximately perpendicularly through a selected one of the apertures to the position illustrated in FIG. 3. After the insertion is completed, the end portion and tongue are returned to their normal planar positions to produce the result illustrated in FIG. 4. The other end portion of the suture carrying the tongue 14 and which is in overlapping relationship to the first-mentioned end portion is then similarly twisted to an angle of approximately 90° and its head 18 inserted approximately perpendicularly through an underlying aperture to the position illustrated in FIG. 5. The tongue and adjacent portion of the suture are then returned to their planar positions to produce the final condition of the installed suture diagrammatically illustrated in FIG. 6.

The above-described suture construction fully attains the objects of the invention previously set forth. Of particular importance is the very substantial reduction in the time required for the suturing operation and the consequent reduction in the period to which the patient is subjected to trauma. The individual locking of each end portion of the suture to the body portion ensures maintenance of the suture in place which is also a matter of major importance. Also, the suture may be readily manufactured and at a nominal cost. The apertures in the body portion of the suture, in addition to their function of receiving the tongues at the ends of the suture for interlocking engagement therewith, also perform the desirable function of substantially reducing the weight of the suture. This function may be enhanced by eliminating the unapertured central portion and providing but a single series of apertures, the series extending from points closely adjacent the ends of the suture and for the full length thereof. In such case, as will be understood, the apertures closely adjacent the ends of the suture and in the central portion thereof will, except possibly in unusual situations, serve only the weight-reducing function, the remaining apertures performing the interlocking function.

I claim:

1. A surgical suture for employment in a looped condition with end portions of said suture in lapping relationship, said suture comprising a thin, narrow, flexible metallic strip of surgical steel, and there are means for interlocking each end of said suture to selected portions along said strip when said end portions are in lapping relationship, said means for interlocking being a series of apertures along a portion of said strip and a shouldered tongue on the other portion of said strip adaptable to be inserted in the aperture and maintained in place.

2. A surgical suture as defined in claim 1 wherein said tongue is connected to said strip by narrow neck elements.

3. A surgical suture as defined in claim 2 wherein said apertures are of rectangular configuration with their longest dimension extending longitudinally of said strip, said apertures being dimensioned to receive said shouldered tongue when said tongue is twisted from a planar position to a position at approximately right angles thereto and to thereafter permit rotation of the tongue to a planar position.

4. A surgical suture as defined in claim 1 wherein said strip carries a plastic coating on the surface portions thereof.

5. A surgical suture as defined in claim 4 wherein said plastic coating is a silicone resin.

* * * * *